April 5, 1932. L. BURBANK Plant Pat. 15
PEACH
Filed Dec. 23, 1930
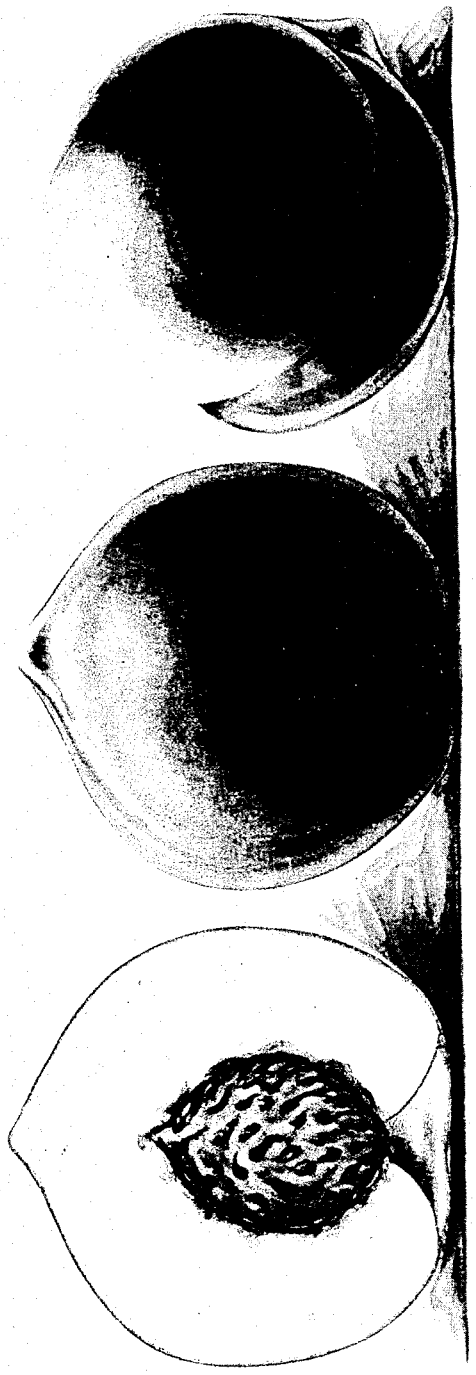
E. W. BURBANK
Executrix of
LUTHER BURBANK, Deceased
By Robb & Robb
ATTORNEYS

UNITED STATES PATENT OFFICE

LUTHER BURBANK, DECEASED, LATE OF SANTA ROSA, CALIFORNIA, BY ELIZABETH WATERS BURBANK, EXECUTRIX, OF SANTA ROSA, CALIFORNIA, ASSIGNOR TO STARK BRO'S NURSERIES & ORCHARDS COMPANY, OF LOUISIANA, MISSOURI

PEACH

Application filed December 23, 1930. Serial No. 504,399.

This invention relates to a new and distinct variety of peach.

This new variety of peach has resulted from years of experimenting with a definite objective in view, that is, to produce a satisfactory yellow freestone peach which ripens half way between the ripening periods of the known varieties, the June Elberta and the Early Elberta. It is similar to the Hale peach except that it has a large pit. Its blood and seed are similar to the Muir, but the fruit is more golden in color. It is a stronger growing tree than the Valient and is not subject to peach curl and disease (Bacteria impruni) as is the last named variety. This new variety produces a very large fruit which averages about one-half pound. Its golden color with maroon shadings modified by a grayish pubescence, adds to its effectiveness in size. Although the skin of the fruit is thin and tender, tests have proven it to be a remarkable shipper; coupled with its great size, impressive coloring, excellent quality, and being a freestone, it represents an outstanding commercial peach. When cut in half, a pleasing modified apricot yellow flesh is disclosed which has a peach red tinge near the pit.

The following specifications and attached drawing show the distinctions and general characteristics of this new variety which has been asexually reproduced.

*Tree*

*Tree.*—The tree, being of vigorous growth, is larger than other varieties of the same age. Its branches are stout, with strong, well knit forks, of divergent habit, with an average angle of 45° to 60°. The bark on the trunk of the young tree forms scales, curling in rather thin flakes, transversely around the trunk. The color is russet brown, modified by light olive gray scarfskin, which, on younger branches has a silvery gloss.

*Twigs.*—The new growth twigs are vigorous and stout, varying to rather slender on lower branches and becoming drooping as growth progresses. The color of the bark of the twigs is glossy courge green minutely dotted with lighter green and shaded vandyke red on exposed side, changing to buckthorn brown on earliest growth of the season. The internodes are short to medium. The dormant fruit buds are medium to large, prominent, free, and dull red-brown with grayish pubescence. The leaf buds are rather small and appressed.

*Foliage.*—The foliage is abundant. The leaves are medium to large, strongly incurved. The texture is thick, soft, and almost velvety. The base is tapering and acute. The blade is flat to distinctly folded, and wrinkled along the midrib. The margin is wavy with a crenate edge having minute reddish points strongly forward. The apex is acuminate to lanceolate. The upper surface is smooth, dull, with slight silvery sheen on oldest leaves. The color is hellebore to courge green. The undersurface is smooth and deep grape green in color.

*Glands.*—There are from two to four large reniform glands, often with additional rudimentary glands on the base of the blade.

*Petiole.*—The petiole is rather short, and is stout. Its color is clear dull green-yellow, extending to midrib and often extensively tinged vandyke red as on the twigs. The upper side is deeply grooved.

*Fruit*

*Form.*—The form is globular with rather broad base and prominent apex producing a broad cordate outline in the longitudinal cross-section. The size is large and uniform, being about three inches axial diameter and three inches largest transverse diameter, and two and three quarters inches smallest transverse diameter, the sides being unequal. The stem is short and moderately stout. The cavity is wide and of medium depth. The suture begins in the cavity, being rather deep at first, becoming a line over the side of the fruit, again more distinct and deep, and ending at the apex which is prominent acute to mammiform.

*Color.*—The color is light orange yellow to capucine orange, largely tinged with minute dots of peach red shading to nopal red and maroon on exposed cheek. The general color effect is somewhat modified by a light to medium persistent grayish pubescence.

*Skin.*—The skin is thin and tender, and is readily removed when the fruit is fully mature.

*Stone.*—The stone is entirely free from the flesh and is medium to rather small as compared with the size of the fruit. The shape of the stone is oval to broadly ovate. Its dimensions are about one and one-half inches long, including the pointed apex, about one and one-eighth inches wide, and one inch thick. The base is wide and somewhat indented or notched. The ventral suture is prominent, rigid, nearly winged, and flanked by a deep furrow on each side. The dorsal suture is a deep narrow groove. The apex is sharply acute, almost acuminate. The sides are deeply convoluted and pitted. The color is pinkish cinnamon when dry.

*Flesh.*—The flesh is moderately firm until mature, whereupon it becomes tender and melting. It is juicy, of fine texture, and slightly fibrous. The color is apricot yellow to light orange-yellow, showing slight marbling on the outer color immediately beneath the skin, and some tinge of peach red in the flesh surrounding the pit. The flavor is a rich subacid mingled with sweet, has a pleasing aroma and is of excellent quality.

(The colors are in accordance with Ridgway's Color Standard.)

The specifications herein set forth the general characteristics of the peach, yet it is understood they may vary slightly due to cultivation and environment.

What is claimed as new is:

The peachtree herein described characterized by the ripening period and color of the skin of its fruit, as shown.

In testimony whereof I affix my signature.

ELIZABETH WATERS BURBANK,
*Executrix of Luther Burbank, Deceased.*